(12) United States Patent  
Kwon et al.

(10) Patent No.: US 8,367,736 B2
(45) Date of Patent: Feb. 5, 2013

(54) ANTICANCER COMPOSITION COMPRISING OBOVATOL OR OBOVATAL

(75) Inventors: Byoung-Mog Kwon, Daejeon (KR); Kwang-Hee Son, Daejeon (KR); Dong-Cho Han, Daejeon (KR); Su-Kyung Lee, Bugi-myeon (KR); Jung-Min Kim, Daejeon (KR); Young-Hee Kho, Daejeon (KR); Hyo-Kon Chun, Daejeon (KR); Jae-Young Yang, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 625 days.

(21) Appl. No.: 12/194,230

(22) Filed: Aug. 19, 2008

(65) Prior Publication Data

US 2008/0312337 A1 Dec. 18, 2008

Related U.S. Application Data

(62) Division of application No. 11/500,013, filed on Aug. 7, 2006, now abandoned.

(30) Foreign Application Priority Data

Aug. 11, 2005 (KR) .................. 10-2005-0073915

(51) Int. Cl.
*A61K 31/11* (2006.01)
(52) U.S. Cl. ........................................ 514/701
(58) Field of Classification Search ........... 514/701
See application file for complete search history.

(56) References Cited

U.S. PATENT DOCUMENTS 5,135,746 A * 8/1992 Matsuno et al. ............. 424/725
2007/0185215 A1 8/2007 Kwon et al.

FOREIGN PATENT DOCUMENTS

KR 1020010001237 5/2001

OTHER PUBLICATIONS

Matsuda et al. (Chem. Pharm. Bull. 2001, 49(6) 716-720).*
Ohshima et al. (Mutation Research, 591, 2005, 110-122, available on line Aug. 3, 2005).*
Azuma et al. (Phytochemistry, 42(4), 1996, 999-1004).*

Dhawan, Subhash, et al., "Interactions between HIV-infected monocytes and the extracellular matrix: HIV-infected monocytes secrete neutral metalloproteases that degrade basement membrane protein matrices", Journal of Leukocyte Biology, Aug. 1992, pp. 244-248, vol. 52.
English Translation of Abstract; Korean Publication No. KR 1020010001237; Applicant: Korea Research Institute of Bioscience and Biotechnology; Published: (May 1, 2001) Abstract Only (2 Pgs).
Ito et al, "Obovatol and Obovatal, Novel Biphenyl Ether Lignans from the Leaves of *Magnolia obovata* Thunb." 1982, 30 (9) 3347-3353.

* cited by examiner

*Primary Examiner* — Kortney L Klinkel
(74) *Attorney, Agent, or Firm* — Casimir Jones, S.C.

(57) ABSTRACT

Disclosed herein is an anticancer composition, comprising obovatol, represented by the following Chemical Formula 1, obovatal, represented by the following Chemical Formula 2, and/or pharmaceutical salts thereof. The composition exhibits the activity of inhibiting the growth of cancer cells and suppressing the expression and activity of matrix metalloproteinases (MMPs), and thus can be useful for the prophylaxis and treatment of cancer as well as for the inhibition of cancer metastasis.

Chemical Formula 1

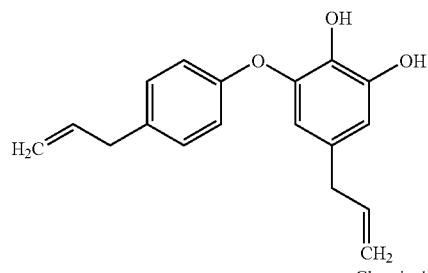

Chemical Formula 2

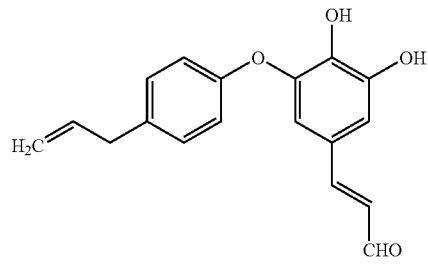

2 Claims, No Drawings

ANTICANCER COMPOSITION COMPRISING OBOVATOL OR OBOVATAL

The present application is a Divisional of U.S. Ser. No. 11/500,013, filed Aug. 7, 2006, which claims priority to Korean Patent Application No.: 10-2005-0073915, filed Aug. 11, 2005.

TECHNICAL FIELD

The present invention relates to an anticancer composition containing obovatol or obovatal as an active ingredient.

BACKGROUND ART

With the great progress of civilization, cancer morbidity has been reported to increase. Despite the increasing incidence of cancer, therapies for cancer still fall within the scope of surgical operation, radiotherapy, and chemical therapies using about 40 chemicals having strong cytotoxicity. However, these therapies are useful only in cancer patients in early stages, or are effective only for certain types of cancer. Despite these therapies, cancer mortality is currently tending to increase.

Death from cancer is mainly due to the metastasis of cancer cells into other tissues rather than due to initial tumors. Active research on the infiltrative and metastatic mechanism of cancer cells and the prevention thereof has been conducted in an effort to reduce cancer mortality.

To metastasize, a cancer cell must break away from the primary tumor, invade support structures of normal tissue, such as interstitial space or capillary basement membranes, to attach to either the circulatory or lymph system, degrade extracellular matrixes and basement membranes, circulate through the bloodstream, and grow at distant loci (metastasize) as a secondary tumor in normal tissues elsewhere in the body, with the concurrent generation of blood vessels (angiogenesis).

Accordingly, the process of metastasis is mainly comprised of attachment, invasion and angiogenesis. If any of them is prevented from happening, cancer metastasis can be prevented. In the invasion of cancer cells, matrix metalloproteinases (MMPs), secreted from the attached cells, are known to play important roles.

MMPs are enzymes involved in the degradation of the extracellular matrix (ECM), such as collagen, proteoglycans, etc, and are represented by, for example, interstitial collagenase, MMP-2, and stromelysin. Also, MMPs, a family of zinc-dependent endopeptidases, must undergo zymogen activation by other proteases or organic phosphorus compounds prior to expressing any proteolytic activity. Their activity is inhibited by TIMP (tissue inhibitor of metalloproteinase) that is secreted together with MMPs. Sharing high cDNA sequence homology, MMPs are collectively classified as a family. MMPs are found to be involved in many pathological conditions, including abnormal connective tissues and basement membrane matrix metabolism, such as tissue ulceration, abnormal wound healing, periodontal disease, bone disease, tumor metastasis or invasion as well as HIV infection (J. Leuk. Biol., 52 (2): 244-248, 1992). In fact, cancer cells, which actively metastasize, show high activity of MMP2 or MMP9, compared to normal cells or non-metastatic cancer cells, and inhibitors of the MMPs are shown to prevent cancer metastasis.

With this background, the present inventors succeeded in isolating and purifying obovatol and obovatal from Magnoliaceae (*Magnolia obovata* Thunberg), which has been used as a herbal medicine, and found that such compounds have the activity of inhibiting the expression and enzymatic activity of MMPs, which play pivotal roles in the growth and metastasis of various human cancer cells.

DISCLOSURE OF THE INVENTION

Accordingly, the present invention has been made keeping in mind the above problems occurring in the prior art, and an object of the present invention is to provide an anticancer composition containing obovatol, represented by the following Chemical Formula 1, and/or obovatal, represented by the following Chemical Formula 2, as a therapeutically active ingredient.

Another object of the present invention is to provide a method for the prophylaxis, treatment and/or metastatic inhibition of cancers using an anticancer composition containing obovatol, represented by the following Chemical Formula 1, and/or obovatal, represented by the following Chemical Formula 2, as a therapeutically active ingredient.

A further object of the present invention is to provide a method for isolating and purifying obovatol and obovatal, represented by the following Chemical Formulas 1 and 2, respectively, from magnoliacea.

BEST MODE FOR CARRYING OUT THE INVENTION

In one embodiment, the present invention provides an anticancer composition containing obovatol, represented by the following Chemical Formula 1, obovatal, represented by the following Chemical Formula 2, or pharmaceutically acceptable salts thereof.

Chemical Formula 1

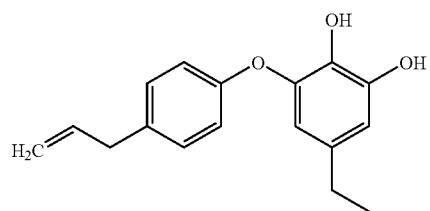

Chemical Formula 2

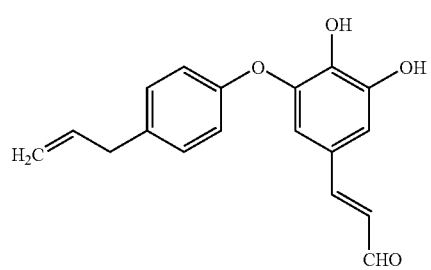

Obovatol and/or obovatal, as an active ingredient of the composition, is found to effectively inhibit the expression and enzymatic activity of MMPs as well as the growth of cancer cells, in accordance with the present invention. Also, the administration of obovatol or obovatal via, for example, the oral route results in the inhibition of cancerous tissues as identified in immune deficient mice into which rectal cancer cells have been transplanted. With the anticancer effect of obovatol or obovatal, which is previously mentioned nowhere, the composition of the present invention is useful for the prophylaxis and treatment of cancer or the inhibition of cancer metastasis.

The term "anticancer", as used herein, is intended to refer to the activity of suppressing the formation or growth of cancer cells, killing cancer cells, or inhibiting or blocking the metastasis of cancer cells, encompassing the meaning of the inhibition of cancer cell metastasis as well as the prophylaxis and treatment of cancer.

The term "prophylaxis" as used herein is intended to mean all actions intended to suppress the formation of cancer or retard cancer incidence by administering the composition. In the present invention, the term "treatment" is intended to mean all actions intended to improve or beneficially modify symptoms of the diseases by administering the composition.

The composition of the present invention can be preferably applied to large intestine cancer, stomach cancer, prostate cancer, breast cancer, kidney cancer, liver cancer, encephaloma, lung cancer, uterine cancer, colon cancer, bladder cancer, pancreatic cancer, and blood cancer for the prophylaxis, treatment or metastatic inhibition thereof, but are not limited thereto.

For use in the composition of the present invention, the compounds of Chemical Formulas 1 and 2 may be in the form of their salts, including various pharmaceutically or physiologically acceptable organic or inorganic acid addition salts. Suitable as inorganic acids for forming salts are hydrochloric acid, sulfuric acid and phosphoric acid. Examples of suitable organic acids include carboxylic acid, phosphonic acid, sulfonic acid, acetic acid, propionic acid, octanoic acid, decanoic acid, glycolic acid, lactic acid, fumaric acid, succinic acid, adipic acid, malic acid, tartaric acid, citric acid, glutamic acid, aspartic acid, maleic acid, benzoic acid, salicylic acid, phthalic acid, phenylacetic acid, benzene sulfonic acid, 2-naphthalenesulfonic acid, methyl sulfuric acid, ethyl sulfuric acid, and dodecyl sulfuric acid.

In the composition of the present invention, the compounds of Chemical Formula 1 and 2 or their salts may be used alone or in combination with one another and optionally in combination with pharmaceutically and physiologically acceptable additives such as carriers, expedients, diluents, etc.

According to the intended administration and usage, the composition of the present invention may be prepared into enteral formulations, such as powders, granules, tablets, capsules, suspensions, emulsions, syrup, aerosol, etc., or parenteral formulations, such as sterile injection solutions, and may be administered orally or injected via various routes, such as intravenous, intraperitoneal, subcutaneous, rectal, local, etc., routes. Examples of carriers, expedients or diluents suitable for use in the composition include lactose, dextrose, sucrose, sorbitol, xylitol, erythritol, maltitol, starch, acacia gum, alginate, gelatin, calcium phosphate, calcium silicate, cellulose, methyl cellulose, non-crystalline cellulose, polyvinyl pyrrolidone, water, methylhydroxybenzoate, propylhydroxybenzoate, talc, magnesium stearate, and mineral oils. Optionally, the composition may further comprise fillers, anti-aggregates, lubricants, wetting agents, flavors, emulsifying agents, preservatives, etc.

Solid formulations suitable for oral administration include tablets, pills, powders, granules, capsules, etc. and may be formulated with at least one expedient, such as calcium carbonate, sucrose, lactose, gelatin, etc. In addition to these, a lubricant, such as magnesium stearate, talc, etc., may be contained in the composition of the present invention.

Liquid formulations suitable for oral administration, exemplified by suspensions, peroral solutions, emulsions, syrup, etc., may comprise various expedients, such as wetting agents, sweetening agents, flavors, preservatives, as well as simple diluents such as water, liquid paraffin, etc.

As for non-oral formulations, sterile aqueous solutions, non-aqueous solutions, suspensions, emulsions, lyophilized injections, suppositories, etc. may be exemplary. Non-aqueous solutions and suspensions may contain propylene glycol, polyethylene glycol, vegetable oil such as olive oil, and injectable esters such as ethylolate.

In another embodiment, the present invention provides a method for the prophylaxis, treatment and/or metastatic inhibition of cancer by the administration of obovatol of Chemical Formula 1, obovatal of Chemical Formula 2, and/or pharmaceutically acceptable salts thereof to patients.

As used herein, the term "administration" is intended to refer to the provision of the substance of interest in a suitable manner into the bodies of the patients. Administration routes of the composition of the present invention are not limited if they lead the active ingredient of the composition to the tissue of target, for example, orally or parenterally. In addition, the composition of the present invention may be administered with the aid of a device for guiding the active ingredient to target cells.

The term "patients", as used herein, is intended to mean subjects whose symptoms are to be improved when administered with the composition of the present invention, including humans and animals, such as anthropoids, dogs, goats, pigs, rats, mice and the like. Accordingly, the composition of the present invention can be provided not only for humans, but is also applicable to animals (for the purpose of the prophylaxis, treatment, and metastatic inhibition of cancer).

The composition of the present invention is administered in a pharmaceutically effective amount. The term "pharmaceutically effective" means sufficient to treat diseases at reasonable ratios of beneficence to danger for medicinal therapy. Dosages of the compound of the present invention depend on the kind and severity of diseases, activity of the drug, sensitivity to the drug, frequency and time period of administration, administration routes, excretion rates, and factors well known in the art including, for example, concurrently used drugs, etc. The composition of the present invention may be used as a single medicine or in combination with other medicines concurrently or sequentially, and may be administered in single dosages or multiple dosages. Taking into account the elements mentioned above, it is important to determine the dosage that elicits maximum therapeutic effects without undesirable side effects, which is easy for those skilled in the art.

Depending on patients' age, sex, and weight, the compound according to the present invention may be administered in a total dosage from 1 to 50 mg per kg of weight, and preferably in a dosage from 1 to 10 mg per kg of weight, once or three times a day. Administration may be conducted every day or every other day. However, because dosages may vary with the administration route, disease severity, gender, weight, age, etc., it must be understood that the above-mentioned dosage does not limit the scope of the present invention.

Obovatol, of Chemical Formula 1, or obovatal, of Chemical Formula 2, may be prepared by being isolated from natural sources or by being synthesized using well-known methods. As a natural source for the compound of Chemical Formula 1 or 2, silver magnolia is preferably used.

Silver magnolia [*Magnolia obovata* Thunberg], belonging to a Magnoliaceae family, is a deciduous tree about 5 m tall, which grows naturally in Korea, Japan, and China.

In herbal medicine, dried cortexes from silver magnolia have been used for the treatment of stomach diseases. Much has been reported about the various physiological activities of honokiol and magnolol, which can be extracted from leaves and cortexes of magnolia, but nowhere has the anticancer effect of obovatol and obovatal from magnolia been mentioned in previous literature.

In a further embodiment, the present invention is concerned with a method for purifying obovatol and obovatal, comprising the steps of (1) extracting obovatol and obovatal from magnolia using alcohol; (2) subjecting the extract of step (1) to silica gel chromatography to yield eluates; (3) subjecting the eluates of step (2) to thin layer chromatography; and (4) subjecting fractions of step (3) to high performance liquid chromatography.

In the alcohol extraction step, leaves, fruit, bark, or all of them may be used. For use in extraction, the alcohol is not specifically limited, but is preferably methanol.

In an example, the extract from leaves, bark and fruit in methanol is loaded on a silica gel chromatography column and eluted with ethyl acetate and hexane to obtain active fractions. Next, thin layer chromatography is conducted by adsorbing the active fractions onto a C18 chromatography column and eluting with methanol and water. High performance liquid chromatography using a methanol:water gradient of preferably 50:50 to 70:30 as an eluent results in the purification of the compound with high purity.

The purified compound was found to be obovatol or obovatal, as measured by UV absorbance, IR absorbance, high resolution mass analysis, and NMR analysis.

A better understanding of the present invention may be obtained through the following examples which are set forth to illustrate, but are not to be construed as the limit of the present invention.

Example 1

Extraction and Purification of Obovatol and Obovatal from Magnolia

Magnolia leaves, fruit, or bark (taken from trees naturally growing in the central region of Korea) were cut into pieces, and allowed to stand for 48 hours at room temperature while being immersed in methanol. Using filter paper, solids were filtered out. After being pooled, the liquid extract was concentrated in a vacuum, and the concentrate was dissolved in methanol.

The organic layers containing active substance were collected and concentrated in vacuo. The concentrate was dissolved in methylene chloride and placed on a silica gel (Merck, Art No. 9385) to adsorb the active substance thereonto. Silica gel column chromatography was conducted with an ethylacetate-hexane gradient varying from 90:10 to 80:20, so as to yield active fractions.

After the adsorption of the fractions onto a C18 column, elution with methanol and water led to the partial purification of the active substance, which was further purified to completion through silica gel column chromatography.

Upon methanol extraction with 2 kg of leaves, about 120 g of the extract was obtained, from which obovatol and obovatal were yielded in amounts of 25 g and 1.5 g, respectively.

Example 2

Structural Analysis of the Purified Compounds

The compounds purified in Example 1 were analyzed for their molecular weights and molecular formulae by analyses including UV absorbance, IR (infrared) absorbance and high resolution mass spectrometry. In detail, a UV-265 spectrophotometer (Shimadzu) was used for UV absorbance analysis, a Digilab Division FTS-80 spectrophotometer (Bio-Rad) for IR absorbance analysis, and high resolution VG70-SEQ mass spectrometry (MS) for the determination of molecular weight and molecular formula. Also, $^1$H and $^{13}$C-NMR spectra were obtained using a nuclear magnetic resonator (Varian 300 MHz, 500 MHz NMR) and analyzed to determine the structures of the compounds.

Physical and chemical properties are given in Table 1 for obovatol and Table 2 for obovatal.

Obovatol $^1$H-NMR (CDCl$_3$): 6.28 (H-4, d, J=1.8 Hz), 6.56 (H-6, d, J=1.8 Hz), 3.18 (H-7, d, J=6.6 Hz), 5.97 (H-8 and H-8', m), 5.09 (H-9 and H-9', m), 6.93 (H-2' and H-6', d, J=9 Hz), 7.14 (H-3' and 5', d, J=9 Hz), 3.36 (H-7', d, J=6.6 Hz).

Obovatal $^1$H-NMR (CDCl$_3$): 9.35 (H-9, d, J=7.5 Hz), 7.38 (H-7, d, J=15.3 Hz), 7.07 (H-3' and H-5', d, J=9 Hz), 6.98 (H-4, d, J=1.8 Hz), 6.78 (H-2' and 6', d, J=9 Hz), 6.75 (H-6, d, J=1.8 Hz), 6.42 (H-8, dd, J=7.5, 15.3 Hz), 4.51 (H-8', m), 5.09 (H-9', m), 3.30 (H-7', d, J=6.6 Hz).

TABLE 1

| Appearance | | pale green |
|---|---|---|
| Empirical Molecular Formula | | $C_{18}H_{18}O_3$ |
| Mw | | 282 |
| m.p. (° C.) | | Liquid |
| Solubility | Soluble | Alcohol, DMSO |
| | Insoluble | Hexane, $H_2O$ |

TABLE 2

| Appearance | | Pale yellow |
|---|---|---|
| Empirical Molecular Formula | | $C_{18}H_{16}O_3$ |
| Mw | | 280 |
| m.p. (° C.) | | 161-162° C. |
| Solubility | Soluble | Alcohol, DMSO |
| | Insoluble | $H_2O$ |

Example 3

Inhibition of Growth of Cancer Cell Strain

The compounds isolated and purified in Example 1 were assayed for their ability to inhibit the growth of cancer cell strains using WST-1. Human cancer cell strains were cultured in media supplemented with 10% FBS in an incubator at 37° C. under 5% $CO_2$ atmosphere, and cell cultures were split when they reached confluence, using 0.05% trypsin-EDTA.

After the determination of cell number using a hematocytometer, cells were placed in each well of 96-well plates at densities of 4,000 cells (A549, MDA-MB-231), 5,000 cells (HEK293, NCI-H23) and 6,000 cells (HCA-7, HCT116, SW620, DU145).

24 hours after incubating the cells in a medium supplemented with 10% FBS in a 37° C. 5% $CO_2$ incubator, the medium was changed with fresh medium containing a control (0.1% DMSO) or various concentrations of the compounds purified in Example 1 (solutions of the compounds in DMSO were diluted with the medium). After incubation for 48 hours, the addition of 10 μl of WST-1 (Roche) to each well was followed by incubation for 2 hours. Absorbance at 450 mm was measured using an ELISA reader (Bio-Rad).

ELISA analysis indicated that when used in an amount from 5 to 15 μg/ml, the compounds of the present invention inhibited the growth of cancer cells by 50%, and were effective for different cancer cell strains. Obovatol was found to have the most inhibitory activity against human large intestine cancer cells HCT116 and HCA-7, as indicated by measured $GI_{50}$ values of 5 μg/ml and 6 μg/ml respectively. On the other hand, obovatol was measured to have a $GI_{50}$ value of 10 μg/ml against SW620 (a colon carcinoma), 20 μg/ml and 25 μg/ml against NCI-H23 and A549 (both lung cancer), respectively, 18 μg/ml against DU145 (prostate cancer), 31 μg/ml against MDA-MB-231 (breast cancer), and 25 μg/ml against HEK293 (kidney cancer). As for obovatal, its $GI_{50}$ values were measured to be 7, 10 and 13 μg/ml against HCT116, HCA-7, SW620 (all colon carcinoma cells), respectively, 11 and 17 μg/ml against NCI-H23 and A549 (both lung cancer), respectively, 20 μg/ml against MDA-MB-231 (breast cancer), and 21 μg/ml against HEK293 (kidney cancer).

Example 4

Determination of Ability of Obovatol and Obovatal to Inhibit Expression of MMP9

The human fibrosarcoma HT1080 was incubated overnight at a density of $1\times10^5$ cells/ml in each well of 96-well plates containing a medium supplemented with 10% FBS, followed by exchange of the medium with a fresh serum-free medium. Three hours after treatment with samples, the cells were treated with 5 ng/ml of tumor necrosis factor α (TNF-α) and then incubated for 17 hours.

Observations were made of cell morphology and cytotoxicity. Only supernatants of the cell cultures were mixed with a storage buffer containing glycerol and a chromogenic reagent and subjected to electrophoresis, which indicated that MMP-9 expression was greatly inhibited in the treated cells compared to the control. TNF-α, acting as an inducer to activate cancer cells in the control, was monitored with the naked eye for its induction behaviors in treated and non-treated cells. In the culture media treated with the samples, a reduced level of MMP-9 was detected as measured by SDS-PAGE.

According to data, obovatol and obovatal inhibited the expression of MMP9 by 50% or more at concentrations of 10 and 5 μg/ml, respectively.

Example 5

Determination of Ability of Obovatol and Obovatal to Inhibit Expression of MMP2

The pro-enzyme MMP2 was activated with 0.5 mM ρ-aminophenylmercuric acetate (APMA) in a reaction buffer at 37° C. for 15 min, and then measured for reaction rate in TNBC buffer (20 mM Tris-HCl, 5 mM $CaCl_2$, 0.15 M NaCl, pH 7.5), with 7-methoxycoumarin-4-yl-acetyl-Pro-Leu-Gly-Leu-(2-[2,4-dinitrophenyl]-2,3-diaminopropionyl)-Ala-Arg-$NH_2$ (Mca-Pro-Leu-Gly-Leu-Dpa-Ala-Arg-$NH_2$) serving as a substrate.

While reacting with the substrate, samples treated with obovatol and obovatal were measured at regular intervals for absorbance at 480 nm. Comparison with control showed that obovatol and obovatal inhibited the activity of MMP2 by 50% or more at concentrations of 0.3 and 90 μg/ml, respectively.

Example 6

Acute Oral Toxicity Assay in Rats

Using six-week-old specific pathogen-free (SPF) SD rats, an acute toxicity assay was conducted. The rats were divided into groups, each consisting of two rats. After being dissolved in injectable saline, the obovatol or obovatal obtained in Example 1, was orally administered once in a dosage of 1 g/kg/ml to the rat groups. Afterwards, observations were made of the death, clinical symptoms, and weight changes of the animals, and serological and serobiochemical assays were conducted. Also, an autopsy was carried out to examine abnormalities of abdominal and thoracic organs with the naked eye.

None of the animals to which the compounds of interest were administered exhibited noticeable clinical symptoms or died. Cytotoxicity was not observed in the weight change, serological assay, serobiochemical assay, or autopsy observations for the animals administered with the compounds of the present invention.

Causing no toxic effects to a dose of 500 mg/kg, both obovatol and obovatal, purified according to the present invention, were determined to have an oral lethal dose ($LD_{50}$) of 500 mg/kg and thus be regarded as safe.

INDUSTRIAL APPLICABILITY

As described hereinbefore, obovatol, represented by Chemical Formula 1, and obovatal, represented by Chemical Formula 2, exhibit activity of inhibiting the growth of cancer cells and suppressing the expression and activity of matrix metalloproteinases (MMPs), and thus can be useful for the prophylaxis and treatment of cancer as well as for the inhibition of cancer metastasis.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for the treatment of cancer, comprising administering to a subject diagnosed with cancer an anticancer composition comprising obovatal, represented by the following Chemical Formula 2, or a pharmaceutical salt thereof, wherein said administering results in the inhibition of growth of said cancer, and wherein said cancer is selected from the group consisting of large intestine cancer, lung cancer, breast cancer and kidney cancer Chemical Formula 2

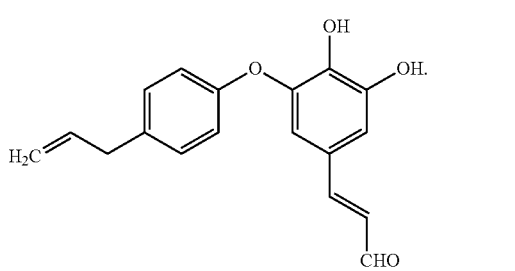

2. A method for inhibiting the metastasis of cancer, comprising administering to a subject diagnosed with cancer an anticancer composition comprising obovatal, represented by the following Chemical Formula 2, or a pharmaceutical salt thereof, wherein said administration results in the inhibition of metastasis of said cancer, and wherein said cancer is selected from the group consisting of large intestine cancer, lung cancer, breast cancer and kidney cancer Chemical Formula 2

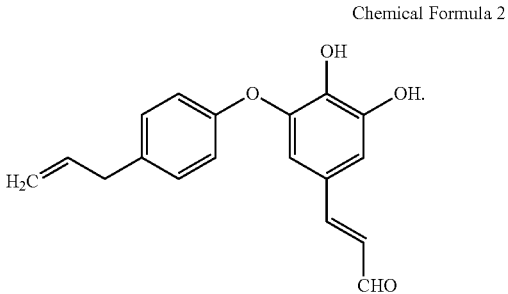 [SMILES: C=CCc1ccc(Oc2cc(/C=C/C=O)cc(O)c2O)cc1]

* * * * *